United States Patent
Schreck

(10) Patent No.: US 7,094,244 B2
(45) Date of Patent: Aug. 22, 2006

(54) SEQUENTIAL HEART VALVE LEAFLET REPAIR DEVICE AND METHOD OF USE

(75) Inventor: Stefan Schreck, Vista, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 472 days.

(21) Appl. No.: 10/106,583

(22) Filed: Mar. 26, 2002

(65) Prior Publication Data

US 2003/0187467 A1    Oct. 2, 2003

(51) Int. Cl.
*A61B 17/04*    (2006.01)

(52) U.S. Cl. .................. 606/139; 606/144; 606/148; 128/898

(58) Field of Classification Search ............... 606/138, 606/139, 144, 148, 150, 153, 213–221, 232, 606/52, 142; 128/898; 604/171, 174–176
See application file for complete search history.

(56) References Cited

U.S. PATENT DOCUMENTS

| | | | |
|---|---|---|---|
| 3,805,793 A | 4/1974 | Wright | |
| 4,350,160 A | 9/1982 | Kolesov et al. | |
| 5,080,663 A | 1/1992 | Mills et al. | |
| 5,242,456 A | 9/1993 | Nash et al. | |
| 5,267,958 A | 12/1993 | Buchbinder et al. | |
| 5,374,275 A | 12/1994 | Bradley et al. | |
| 5,403,326 A | 4/1995 | Harrison et al. | |
| 5,443,446 A | 8/1995 | Shturman | |
| 5,458,131 A | 10/1995 | Wilk | |
| 5,474,573 A | 12/1995 | Hatcher | |
| 5,540,704 A | 7/1996 | Gordon et al. | |
| 5,569,274 A | 10/1996 | Rapacki et al. | |
| 5,573,540 A | 11/1996 | Yoon | |
| 5,575,800 A | 11/1996 | Gordon | |
| 5,578,044 A | 11/1996 | Gordon et al. | |
| 5,601,574 A | 2/1997 | Stefanchik et al. | |
| 5,662,664 A | 9/1997 | Gordon et al. | |
| 5,685,867 A | 11/1997 | Twardowski et al. | |
| 5,695,457 A | 12/1997 | St. Goar et al. | |
| 5,700,272 A | 12/1997 | Gordon et al. | |
| 5,713,910 A | 2/1998 | Gordon et al. | |
| 5,716,367 A | 2/1998 | Koike et al. | |
| 5,741,277 A | 4/1998 | Gordon et al. | |
| 5,741,279 A | 4/1998 | Gordon et al. | |
| 5,766,183 A | 6/1998 | Sauer | |
| 5,792,094 A | 8/1998 | Stevens et al. | |
| 5,792,153 A | 8/1998 | Swain et al. | |
| 5,836,956 A | 11/1998 | Buelna et al. | |

(Continued)

FOREIGN PATENT DOCUMENTS

DE    197 25 739 C    4/1999

(Continued)

*Primary Examiner*—Julian W. Woo
(74) *Attorney, Agent, or Firm*—David L. Hauser; Richard B. Cates

(57) ABSTRACT

A heart valve and tissue repair device for independently, selectively and sequentially grasping heart valve leaflets and independently, selectively and sequentially applying one or more fasteners thereto is disclosed. The device includes a leaflet engaging tip having one or more graspers capable of individually and sequentially grasping leaflets, and one or more deployable fasteners capable of fastening the leaflets. An actuation system for the device individually and selectively controls the graspers and deploys the one or more fasteners. Vacuum pressure from an external vacuum source can be used to grasp the leaflets via a selector system that controls the actuation system so as to individually and sequentially apply vacuum force to the graspers.

21 Claims, 11 Drawing Sheets

U.S. PATENT DOCUMENTS

| | | | |
|---|---|---|---|
| 5,839,639 A | 11/1998 | Sauer et al. | |
| 5,860,992 A | 1/1999 | Daniel et al. | |
| 5,885,238 A | 3/1999 | Stevens et al. | |
| 5,891,159 A | 4/1999 | Sherman et al. | |
| 5,891,160 A | 4/1999 | Williamson et al. | |
| 5,924,424 A | 7/1999 | Stevens et al. | |
| 5,928,224 A | 7/1999 | Laufer | |
| 5,928,250 A | 7/1999 | Koike et al. | |
| 5,968,059 A | 10/1999 | Ellis et al. | |
| 5,972,020 A | 10/1999 | Carpentier et al. | |
| 5,976,159 A * | 11/1999 | Bolduc et al. | 606/142 |
| 6,010,531 A | 1/2000 | Donlon et al. | |
| 6,015,427 A | 1/2000 | Mueller et al. | |
| 6,029,671 A | 2/2000 | Stevens et al. | |
| 6,047,700 A | 4/2000 | Eggers et al. | |
| 6,056,760 A | 5/2000 | Koike et al. | |
| 6,080,182 A | 6/2000 | Shaw et al. | |
| 6,083,219 A | 7/2000 | Laufer | |
| 6,117,159 A | 9/2000 | Huebsch et al. | |
| 6,149,660 A | 11/2000 | Laufer et al. | |
| 6,157,852 A | 12/2000 | Selmon et al. | |
| 6,162,233 A | 12/2000 | Williamson et al. | |
| 6,165,183 A | 12/2000 | Kuehn et al. | |
| 6,190,357 B1 | 2/2001 | Ferrari et al. | |
| 6,234,995 B1 | 5/2001 | Peacock | |
| 6,312,447 B1 | 11/2001 | Grimes | |
| 6,443,922 B1 | 9/2002 | Roberts et al. | |
| 6,508,777 B1 | 1/2003 | Macoviak et al. | |
| 6,575,971 B1 * | 6/2003 | Hauck et al. | 606/52 |
| 6,582,388 B1 | 6/2003 | Coleman et al. | |
| 6,626,930 B1 * | 9/2003 | Allen et al. | 606/213 |
| 6,645,205 B1 | 11/2003 | Ginn | |
| 2002/0049402 A1 | 4/2002 | Peacock et al. | |
| 2003/0130571 A1 | 7/2003 | Lattouf | |

FOREIGN PATENT DOCUMENTS

| | | |
|---|---|---|
| EP | 0570915 A2 | 11/1993 |
| EP | 0769272 A1 | 4/1997 |
| EP | 0861632 A1 | 9/1998 |
| WO | WO 95/15715 | 6/1995 |
| WO | WO 95/25468 | 9/1995 |
| WO | WO 97/27893 | 6/1997 |
| WO | WO 97/27807 | 8/1997 |
| WO | WO 98/57585 | 12/1998 |
| WO | WO 99/00059 | 1/1999 |
| WO | WO 99/13777 A1 | 3/1999 |
| WO | WO 99/15223 | 4/1999 |
| WO | WO 00/03759 | 1/2000 |
| WO | WO 00/59382 | 10/2000 |
| WO | WO 00/60995 | 10/2000 |
| WO | WO 01/26557 | 4/2001 |
| WO | WO01/28432 | 4/2001 |
| WO | WO0128432 | 4/2001 |
| WO | WO0166018 | 9/2001 |
| WO | WO01/95809 | 12/2001 |
| WO | WO 02/24078 | 3/2002 |
| WO | WO02/34167 | 5/2002 |
| WO | WO03/001893 | 1/2003 |

* cited by examiner

SEQUENTIAL HEART VALVE LEAFLET REPAIR DEVICE AND METHOD OF USE

CROSS REFERENCE TO RELATED APPLICATIONS

This application discloses subject matter related to co-pending U.S. patent application Ser. No. 09/562,406, filed May 1, 2000, now U.S. Pat. No. 6,626,930, entitled "Minimally Invasive Mitral Valve Repair Method And Apparatus", and U.S. patent application Ser. No. 09/778,392, filed Feb. 6, 2001, now abandoned, entitled "Method and System for Tissue Repair Using Dual Catheters". The entire disclosures of the aforementioned United States patent applications are incorporated herein by reference.

BACKGROUND OF THE INVENTION

In vertebrate animals, the heart is a hollow muscular organ having four pumping chambers: the left atrium, the left ventricle, the right atrium and the right ventricle. The atria are isolated from their respective ventricles by one-way valves located at the respective atrial-ventricular junctions. These valves are identified as the mitral (or bicuspid) valve on the left side of the heart, and tricuspid valve on the right side of the heart. The exit valves from the left and right ventricles are identified as the aortic and pulmonary valves, respectively.

The valves of the heart are positioned in valvular annuluses that comprise dense fibrous rings attached either directly or indirectly to the atrial and ventricular muscle fibers. Valve leaflets comprising flexible collagenous structures are attached to, and extend inwardly from, the annuluses to meet at coapting edges. The aortic, tricuspid and pulmonary valves each have three leaflets, while the mitral valve only has two. In normal operation, the leaflets of the mitral valve open as left ventricle dilates thereby permitting blood to flow from the left atrium into the left ventricle. The leaflets then coapt (i.e. close) during the contraction cycle of the left ventricle, thereby preventing the blood from returning to the left atrium and forcing the blood to exit the left ventricle through the aortic valve. Similarly, the tricuspid valve regulates flow from the right atrium into the right ventricle, and the pulmonary valve regulates blood exiting the right ventricle.

For a number of clinical reasons various problems with heart valves can develop. One common form of heart disease involves the deterioration or degradation of the heart valves which leads to stenosis and/or insufficiency. Heart valve stenosis is a condition in which the valve does not open properly. Insufficiency is a condition in which the valve does not close properly. Insufficiency of the mitral valve, most common because of the relatively high fluid pressures in the left ventricle, results in mitral valve regurgitation ("MR"), a condition in which blood reverses its intended course and flows "backward" from the left ventricle to the left atrium during heart contractions.

A number of surgical techniques have been developed to repair degraded or otherwise incompetent heart valves. A common procedure involves replacement of a native aortic or mitral valve with a prosthetic heart valves. These procedures require the surgeon to gain access to the heart through the patient's chest (or possibly percutaneously), surgically remove the incompetent native heart valve and associated tissue, remodel the surrounding valve annulus, and secure a replacement valve in the remodeled annulus. While such procedures can be very effective, there are significant shortcomings associated with such replacement valves. For example, the highly invasive nature of the implantation procedure typically results in substantial patient discomfort and requires patients to remain hospitalized for extended recovery periods. In addition, the two basic types of commercially available replacement valves, mechanical valves and tissue valves, each have shortcomings of their own. Mechanical replacement valves typically offer extended operational lifetimes, but the patient is usually required to maintain a regimen of anti-coagulant drugs for the remainder of his or her life. Tissue valves typically offer a higher degree of acceptance by the body which reduces or eliminates the need for anti-coagulants. However, the operational lifetimes of tissue valves are typically shorter than mechanical valves and thus may require a subsequent replacement(s) during the patient's lifetime.

As an alternative to prosthetic heart valve replacement, it is often preferable to remodel the native heart valve and/or surrounding tissue. Remodeling of the valve often preserves left ventricular function better than mitral valve replacement because the subvalvular papillary muscles and chordae tendineae are preserved (most prosthetic valves do not require these muscles to operate). Typically, valvular remodeling is accomplished by implanting a prosthetic ring (a.k.a. "annuloplasty ring") into the valve annulus to reduce and/or stabilize the structure of the annulus in order to correct valvular insufficiency. Annuloplasty rings are typically constructed of a resilient core covered with a fabric sewing material. Annuloplasty procedures can be performed alone, or they can be performed in conjunction with other procedures such as leaflet repair. Although such annuloplasty procedures have become popular and well accepted, reshaping the surrounding annulus and traditional leaflet repairs do not always lead to optimum leaflet coaptation. As a result, some patients may still experience residual mitral valve regurgitation following such annuloplasty procedures.

A recently developed technique known as a "bow-tie" repair has also been advocated for repairing insufficient heart valves, in particular the mitral valve. The mitral valve bow-tie technique involves suturing the anterior and posterior leaflets together near the middle of their coapting edges, thereby causing blood to flow through two newly formed side openings. While this does reduce the volume of blood that can flow from the atrium to the ventricle, this is compensated by improved leaflet coaptation which reduces mitral regurgitation. This process as originally developed by Dr. Ottavio Alfieri involved arresting the heart and placing the patient on extracorporeal bypass and required invasive surgery to access and suture the leaflets together. More recently, however, some have advocated a "beating heart" procedure in which the heart is accessed remotely and remains active throughout the bow-tie procedure.

A particular method for performing a beating heart bow-tie procedure (i.e. without extracorporeal bypass) has been proposed by Dr. Mehmet Oz, of Columbia University. A method and device for performing the method are described in PCT publication WO 99/00059, published Jan. 7, 1999. In one embodiment of the disclosed procedure, the associated device consists of a forceps-like grasper used to grasp and hold the mitral valve leaflets in a coapted position for the suturing step. Since the mitral valve leaflets meet and curve toward and slightly into the left ventricular cavity at their mating edges, the grasper device is passed through a sealed aperture in the apex of the left ventricle. The edges of the mating mitral valve leaflets are then grasped and held together, and a fastening device such as a clip or suture is utilized to fasten them. The fastening devices should be applied to the leaflet tissue with sufficient tissue purchase to prevent tearout or other failure, but close enough to the edges to ensure that the newly created side holes are as large as possible. The Mehmet Oz disclosure thus teaches that teeth of the grasper device can be linearly slidable with respect to one another so as to permit alignment of the mitral valve leaflets prior to fastening. Since the procedure is done on a beating heart, it will be readily understood that the pressures and motions within the left ventricle and mitral valve leaflets are severe. Thus the procedure taught by Dr. Mehmet Oz is very skill-intensive.

The bow-tie technique has proved to be a viable alternative for treating otherwise incompetent heart valves. Nonetheless, several shortcomings associated with the current bow-tie procedures have been identified. Current systems include devices having mechanical graspers, barbed members, and vacuum devices that simultaneously capture and retain the valve leaflets prior to applying a fastening device thereto. Often, use of these devices results in the less than optimal leaflet stabilization and fastener placement. Many of these problems arise from the fact that the surgeon is required to capture, retain and fasten the leaflets in one relatively inflexible procedure. These difficulties are compounded when the leaflets are small or calcified making them difficult to pull together, and in beating heart procedures in which the leaflets are actively functioning throughout the surgery. In light of the foregoing, there is presently a need for improved systems for stabilizing multiple tissue heart valve leaflets and placing a fastening device therebetween. More specifically, there is a present need for an improved bow-tie procedure for repairing a patient's mitral valve.

SUMMARY OF THE INVENTION

The present invention provides a device capable of effectively stabilizing at least one heart valve leaflets, or portions of a single leaflet, and applying a fastener thereto. Those skilled in the art will appreciate that the present invention enables a user to apply such a fastener in vivo to a remote location within the patient's heart.

In one aspect, the repair device of the present invention comprises a leaflet engaging tip, a leaflet grasping mechanism positioned on the leaflet engaging tip, a deployable fastener positioned on the leaflet engaging tip, and an actuation system in communication with the grasping mechanism and the fastener. The actuation system has at least two actuation modes and is capable of independently and sequentially operating in each actuation mode. In the first actuation mode the actuation system is capable of causing the grasping mechanism to grasp a first leaflet, deploying a first fastening element into the first leaflet, and subsequently causing the grasping mechanism to release the first leaflet. In the second actuation mode the actuation system is capable of causing the grasping mechanism to grasp a second leaflet, deploying a second fastening element into the second leaflet, and subsequently causing the grasping mechanism to release the second leaflet.

In another aspect, the present invention comprises multiple fasteners having multiple fastening elements and wherein the actuation system is capable of independently and sequentially deploying the multiple fastening elements into the leaflets.

In another aspect, the present invention utilizes an external vacuum source to enable the grasping mechanism to grasp a leaflet by applying vacuum force thereto. In this aspect the grasping mechanism comprises a vacuum port, the actuation system is in fluid communication with both the vacuum port and the vacuum source, and the actuation system is capable of selectively restricting or transmitting vacuum force from the vacuum source to the vacuum port.

In another aspect, the present invention comprises one or more vacuum ports, each having at least one vacuum vane capable of directing vacuum force through the vacuum port while supporting a leaflet attached thereto.

In another aspect, the present invention includes one or more vacuum ports, each having a fastener catch capable of engaging and retaining the fastening elements.

In another aspect, the present invention utilizes an external vacuum source to enable the grasping mechanism to independently and sequentially grasp leaflets by applying vacuum force to multiple vacuum ports. In this aspect the grasping mechanism comprises first and second vacuum ports, the actuation system is in fluid communication with the vacuum ports and the vacuum source. In a first actuation mode the actuation system is capable of selectively restricting or transmitting vacuum force from the vacuum source to the first vacuum port and, in a second actuation mode the actuation system is capable of selectively restricting or transmitting vacuum force from the vacuum source to the second vacuum port.

In a related aspect, the present invention comprises a user-operable selector capable of being placed in a first position that places an actuation system in a first actuation mode and a second position that places the actuation system in the second actuation mode.

In a related aspect, the present invention comprises a user-operable vacuum actuator having an open position in which vacuum force is transmitted from a vacuum source to a selected port and a closed position in which vacuum force is isolated from the ports.

In another aspect, the present invention comprises at least one deployable fastener comprising a length of suture material and fastening elements comprising needles connected to opposite ends of the suture material.

In another aspect, the present invention comprises an actuation system having a user-operable fastener actuator capable of individually and sequentially deploying fastening elements.

In another aspect, the present invention comprises an actuation system coupled to a user-operable selector capable of being placed in multiple positions. In a first position the selector places the actuation system in a first actuation mode, and a second position the selector places the actuation system in a second actuation mode.

In another aspect, the present invention comprises a selector and fastener actuator having a trigger mechanism coupled to a force transmitter. In this aspect, a selector selectively couples the force transmitter with a first or second fastening element.

In another aspect, the present invention comprises at least one deployable fastener selected from the group consisting of needles, sutures, staples, buttons, tissue-graspers, tissue clasps, and barbs.

In another aspect, the present invention comprises an elongated body in communication with a tissue engaging tip, a handle portion in communication with the elongated body, and a user-operable selector coupled to the handle and capable of being placed in multiple positions. Placing the selector in a first position places an actuation system in a first actuation mode; and, placing the selector in a second position places the actuation system in the second actuation mode.

In a related aspect, the present invention comprises a rigid elongated body.

In a related aspect, the present invention comprises a flexible elongated body.

In a related aspect, the present invention comprises an elongated body having at least one conduit therein.

In another aspect, the repair device of the present invention comprises a leaflet engaging tip, at least two leaflet grasping mechanisms positioned on the leaflet engaging tip, at least one deployable fastener having multiple fastening elements positioned on the leaflet engaging tip, and an actuation system in communication with the grasping mechanism and the fastener. The actuation system has at least two actuation modes and is capable of independently and sequentially operating in each actuation mode. In the first actuation mode the actuation system is capable of causing a first grasping mechanism to grasp a first leaflet, deploying a first fastening element into the first leaflet, and subsequently causing the first grasping mechanism to release the first leaflet. In the second actuation mode the actuation system is capable of causing a second grasping mechanism to grasp a second leaflet, deploying a second fastening element into the second leaflet, and subsequently causing the second grasping mechanism to release the second leaflet.

In another aspect, the present invention utilizes an external vacuum source to enable multiple grasping mechanisms to grasp leaflets by applying vacuum force thereto. In this aspect each grasping mechanism comprises a vacuum port, the actuation system is in fluid communication with each vacuum port and the vacuum source, and the actuation system is capable of selectively restricting or transmitting vacuum force from the vacuum source to each vacuum port.

In another aspect, the present invention discloses a method of repairing a heart valve having multiple leaflets. The method includes stabilizing a first leaflet with the repair device, deploying a first fastener element into the stabilized first leaflet, disengaging the first leaflet from the repair device while leaving the first fastener element deployed therein, stabilizing a second leaflet with the repair device, deploying a second fastener element into the second leaflet, disengaging the second leaflet from the repair device while leaving the second fastener element deployed therein, and joining the first and second leaflets by reducing the distance between the first and second fastener elements. Additional leaflet portions may also be attached in a similar manner.

In another aspect, the present invention discloses a method of controllably and selectively stabilizing multiple heart valve leaflets with vacuum force.

In another aspect, the present invention discloses a method of stabilizing multiple heart valve leaflets with a piece of suture material by first fastening the suture material to the leaflets and then tying the suture material into a knot.

In another aspect, the present invention comprises a method of adjusting the position of a repair device relative to a heart valve by monitoring fluid pressure around a distal end of the repair device.

In another aspect, the present invention comprises a method of adjusting the position of a repair device relative to an atrial-ventricular junction by observing pressure differentials between blood in an adjacent ventricle and an adjacent atrium.

Other objects, features, and advantages of the present invention will become apparent from a consideration of the following detailed description.

BRIEF DESCRIPTION OF THE DRAWINGS

The apparatus of the present invention will be explained in more detail by way of the accompanying drawings, wherein.

DESCRIPTION OF THE PREFERRED EMBODIMENTS

Disclosed herein is a description of various illustrated embodiments of the present invention. This description is not to be taken in a limiting sense, but is made merely for the purpose of illustrating the general principles of the invention. The section titles and overall organization of the present description are for the purpose of convenience only and do not limit the present invention.

The methods and devices of the present invention were primarily designed for use in the surgical treatment of heart valves. As those skilled in the art will appreciate, the exemplary sequential repair device disclosed herein is designed to minimize trauma to the patient before, during, and subsequent to a surgical procedure, while providing improved heart valve leaflet stabilization and enhanced placement of a fastening device thereon. The repair device of the present invention is particularly useful in repairing dysfunctional mitral valves by stabilizing the discrete valvular tissue pieces of the anterior and posterior leaflets and deploying a fastening device(s) thereto.

Figure 1:
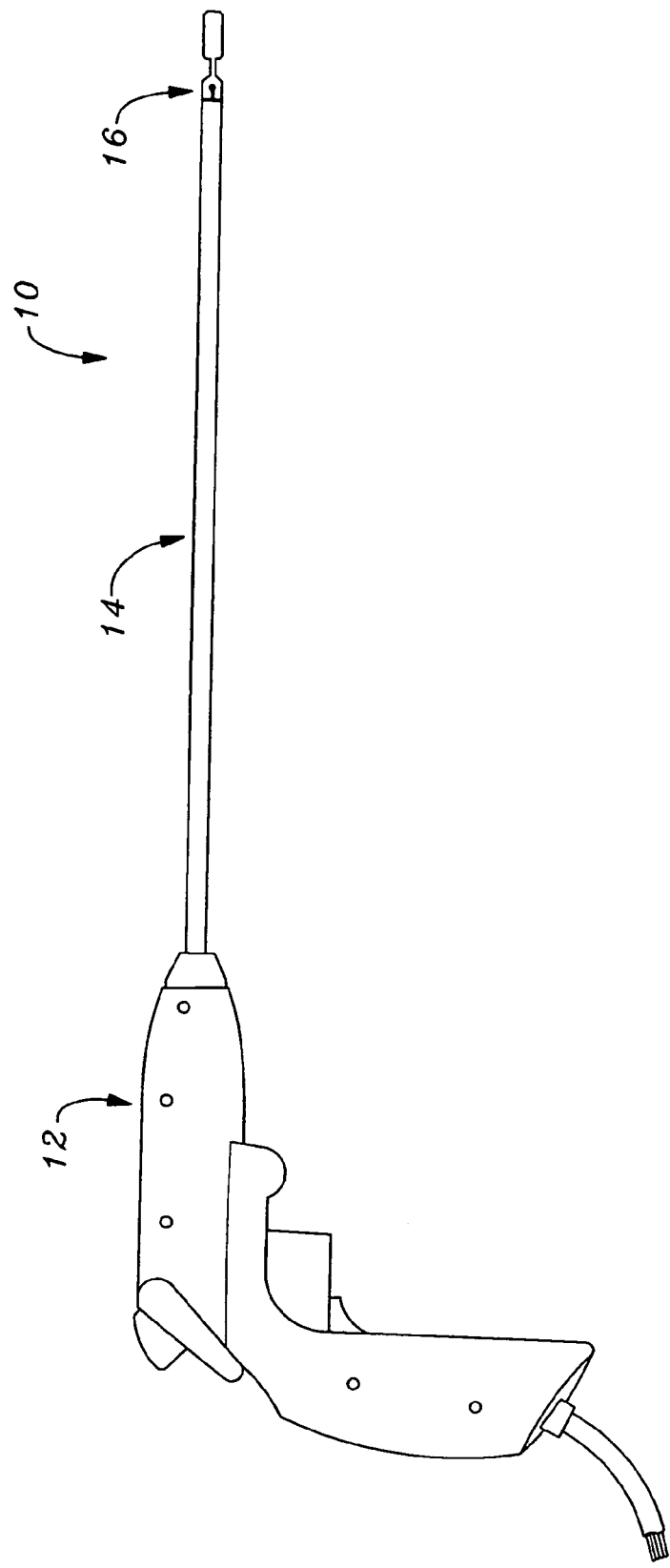
FIG. 1 shows a perspective view of the repair device of the present invention.

FIG. 1 shows the sequential repair device of the present invention. As illustrated, the repair device 10 comprises a handle portion 12 in communication with an elongated body 14. A leaflet engaging tip 16 is positioned on the distal portion of the elongated body 14. Those skilled in the art will appreciate that the present invention may be manufactured from a plurality of materials including, without limitation, various metals, plastics, thermoplastics, silicones, elastomers, ceramics, composite materials, or various combinations of the aforementioned materials. For example, the handle portion 12 may be manufactured from acrylic, while the elongated body 14 may be manufactured from stainless steel.

Figure 2:
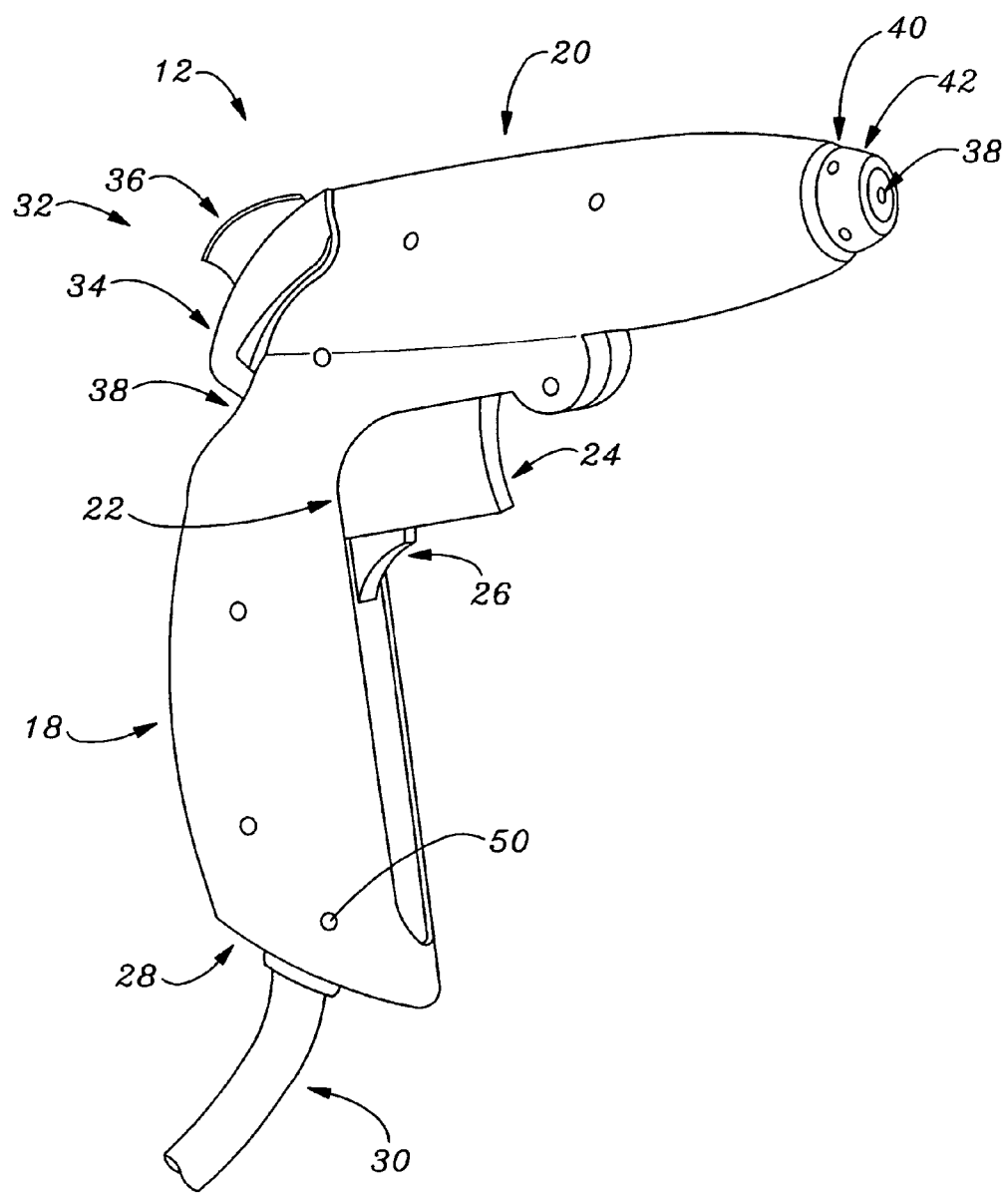
FIG. 2 shows a perspective view of handle portion of the repair device of the present invention.

FIG. 2 shows a perspective view of the handle portion 12. As shown in FIG. 2, the handle portion 12 comprises a grip portion 18 in communication with a housing body 20. The grip portion 18 includes a trigger recess 22 capable of receiving a trigger 24 therein. A trigger guide 26 is positioned proximate to the trigger recess 22. In addition to supporting the trigger 24, the trigger guide 26 isolates the trigger 24 from the grip portion 18 thereby preventing the accidental actuation of the trigger 24. In one embodiment, the grip portion 18 is perpendicularly attached to the housing body 20, thereby forming a pistol-type grip. Those skilled in the art will appreciate that the handle portion 14 of the present invention may be manufactured in a plurality of shapes as desired by the operator. At least one external conduit recess 28 capable of receiving at least one external conduit 30 therein may be formed on the repair device 10.

The handle portion 12 further comprises a vacuum actuator recess 32 capable of receiving a vacuum actuator 34 and a vacuum selector 36 therein. As shown in FIG. 2, the vacuum actuator recess 32 may be positioned adjacent to the trigger recess 22 thereby permitting the user to single-handedly operate the vacuum actuator 34, the vacuum selector 36, and the trigger 24 simultaneously. In an alternate embodiment, the vacuum actuator recess 32 may be positioned remotely from the trigger recess 22 to prevent the accidental actuation of the vacuum actuator 34 or the vacuum selector 36.

An elongated body aperture 38 capable of receiving the elongated body 14 therein is formed in the housing body 20. At least one coupling member receiver 40 capable of receiving at least one coupling member 42 therein is formed in the housing body 20 proximate to the elongated body aperture 38 to effect coupling of the elongated body 14 to the handle portion 12. Those skilled in the art will appreciate that the at least one coupling member 42 may include, without limitation, screws, rivets, pins, or locking members, thereby permitting the elongated body 14 to be detachable from the handle portion 12. In another embodiment, the elongated body 14 may be permanently attached to handle portion 12 with in a plurality of ways, such as welding or gluing.

Figure 3:
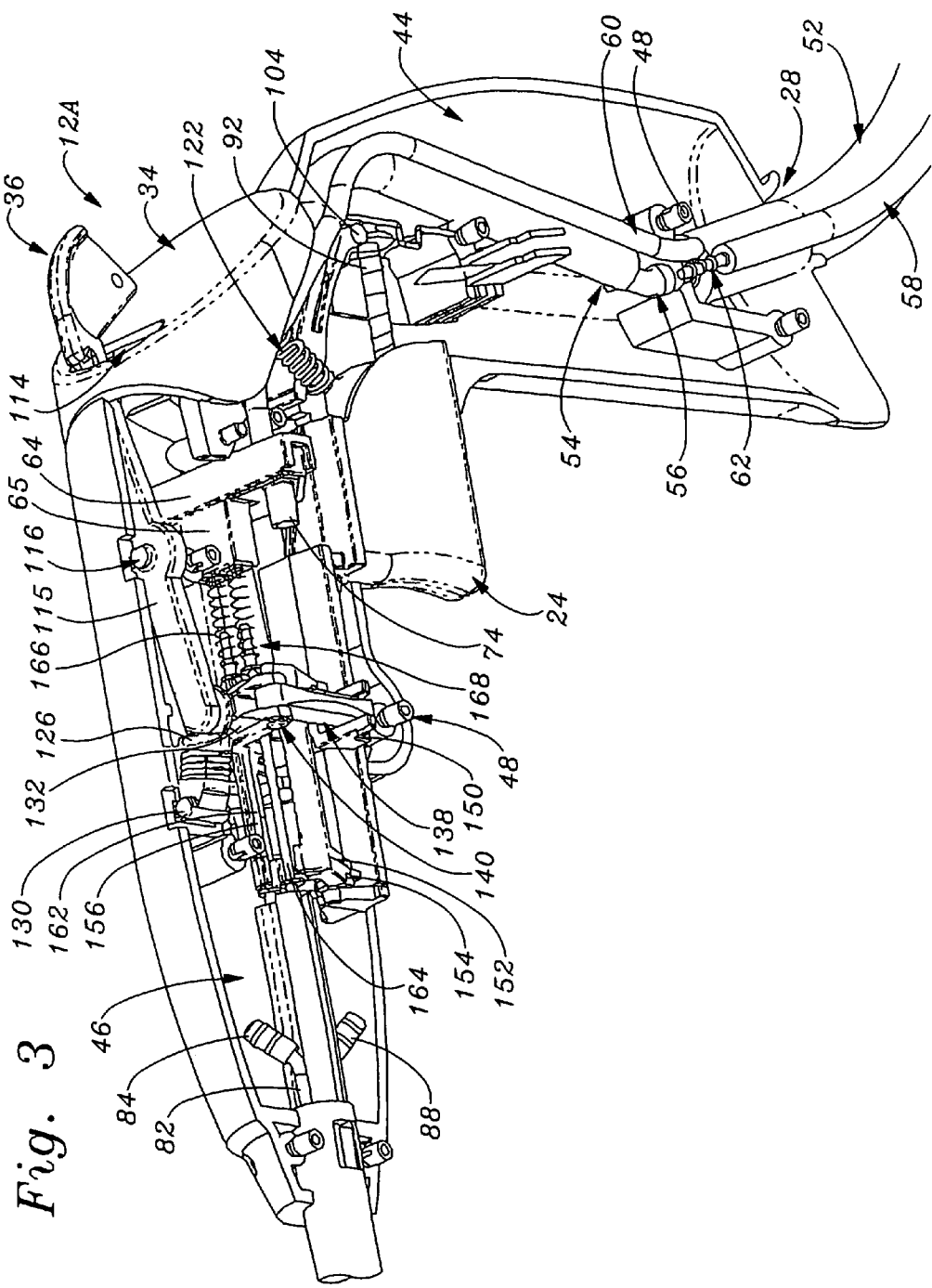
FIG. 3 shows a perspective cross-sectional view of the internal components located within the handle portion of the repair device of the present invention.
Figure 7:
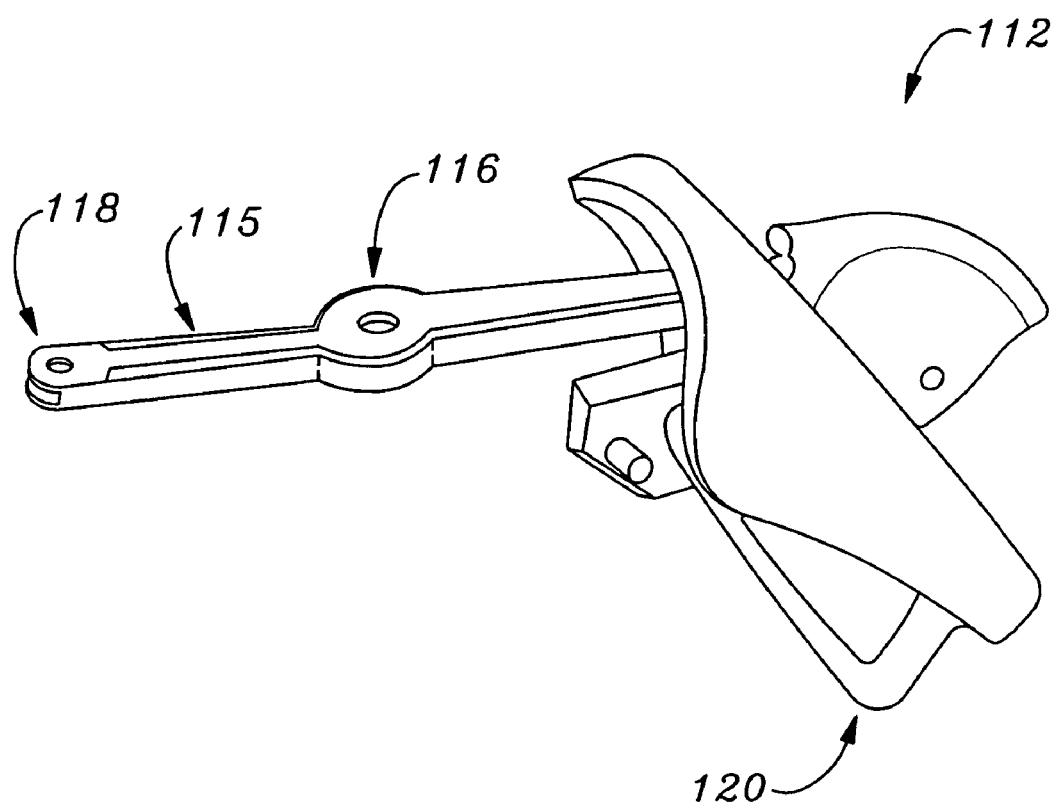
FIG. 7 shows a perspective view of the vacuum actuation assembly of the repair device of the present invention.

FIGS. 3 and 7 show the internal components in more detail. As shown in FIG. 3 the handle portion may be split into two hollow halves comprising a first handle portion 12A and a second handle portion 12B which cooperatively form a handle cavity 44 and a housing cavity 46 within the handle portion 12. At least one assembly device receiver 48 capable of receiving at least one assembly device (not shown) therein may be formed, e.g. molded, in the first and/or second handle portions 12A, 12B. Exemplary assembly devices include, but are not limited to, screws, rivets, assembly pins or adhesives.

Figure 4:
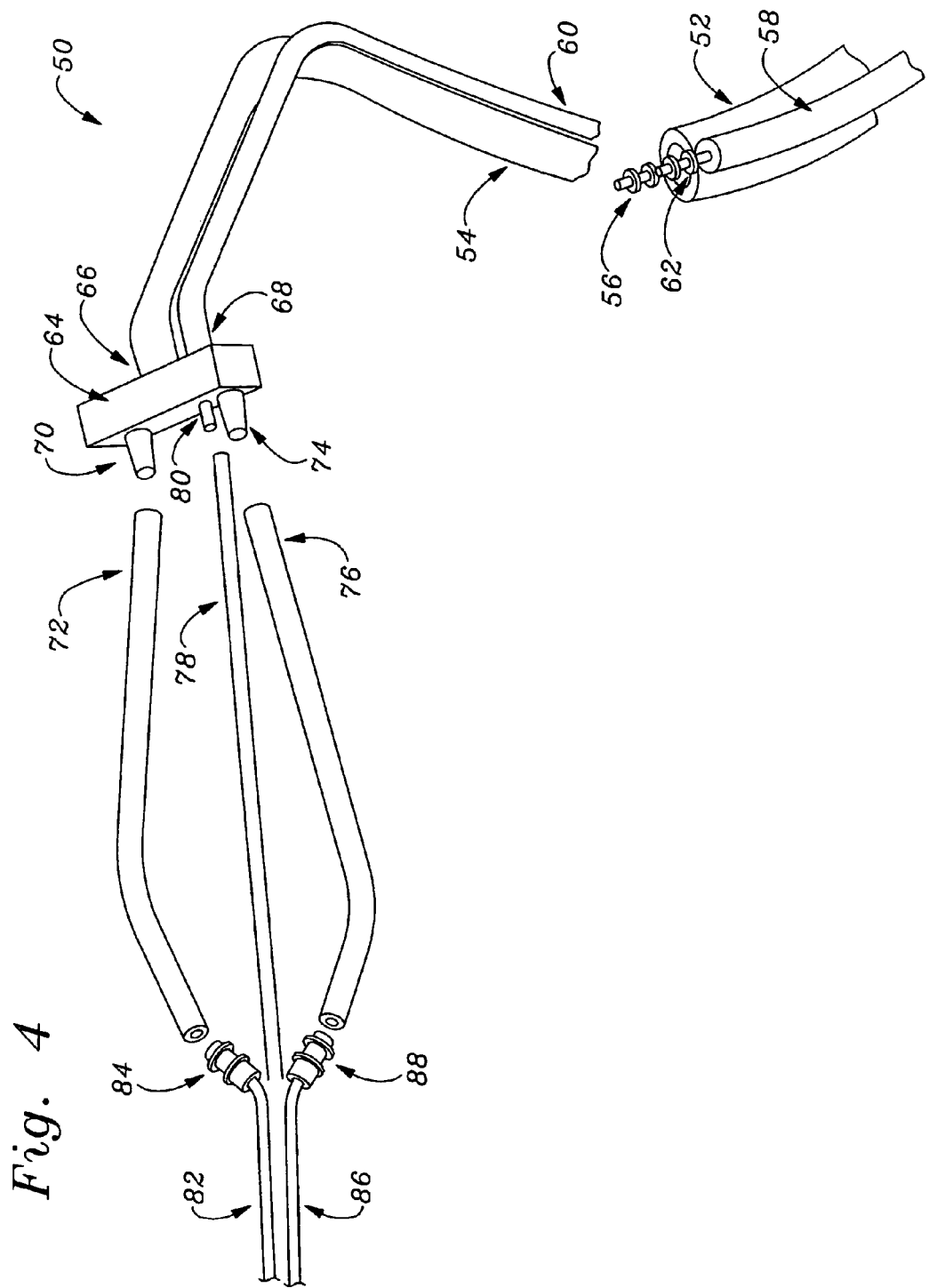
FIG. 4 shows a perspective view of the vacuum system of the repair device of the present invention.

FIGS. 3 and 4 show vacuum system 50. An external vacuum conduit 52, positioned within the at least one external conduit recess 28 formed in the repair device 10, is attached to a compressible main vacuum line 54 through a vacuum coupler 56. The external vacuum conduit 52 is in communication with a vacuum source (not shown), thereby providing suction (i.e. vacuum pressure) to the repair device 10. In addition, an external positioning conduit 58 is positioned within the at least one external conduit recess 28 and is attached to an internal positioning line 60 through a positioning coupler 62. The external positioning conduit 58 may be in communication with a positioning system. In one embodiment, the external positioning conduit 58 may be in communication with a pressure sensing device. Those skilled in the art will appreciate that a pressure sensing device can be used to assist the user in the precise placement of the repair device 10 within the patient based on a determination of pressure levels within the various parts of the body. For example, such a pressure sensing system would assist the user in determining the position of the leaflet engaging tip 16 of the repair device 10 relative to the atrial-ventricular junction of the patient's heart by sensing variations in the internal pressure between the atrium and the ventricle. In other embodiments, the present invention may be easily adapted to utilize a plurality of alternate positioning systems, including, without limitation, optical systems, ultrasonic systems, echogenic systems, microwave positioning systems, radio-frequency positioning systems, or radio-opaque positioning devices.

As shown in FIGS. 3 and 4, the main vacuum line 54 is attached to a vacuum manifold 64 through a vacuum coupler 66. The internal positioning line 60 is similarly attached to the vacuum manifold 64 through a positioning line coupler 68. The vacuum manifold 64 includes a first vacuum conduit coupler 70 capable of coupling to a first vacuum conduit 72 and a second vacuum conduit coupler 74 capable of coupling to a second vacuum conduit 76 thereby permitting the first and second vacuum conduits 72, 76 to communicate with the main vacuum line 54. A positioning conduit 78 is attached to the vacuum manifold 64 through a positioning coupler 80, thereby permitting the positioning conduit 78 to communicate with the internal positioning line 60. The first vacuum conduit 72 attaches to the first elongated body vacuum conduit 82 through a coupling member 84. Similarly, the second vacuum conduit 76 is attached to a second elongated body vacuum conduit 86 through a coupling member 88.

Figure 5:
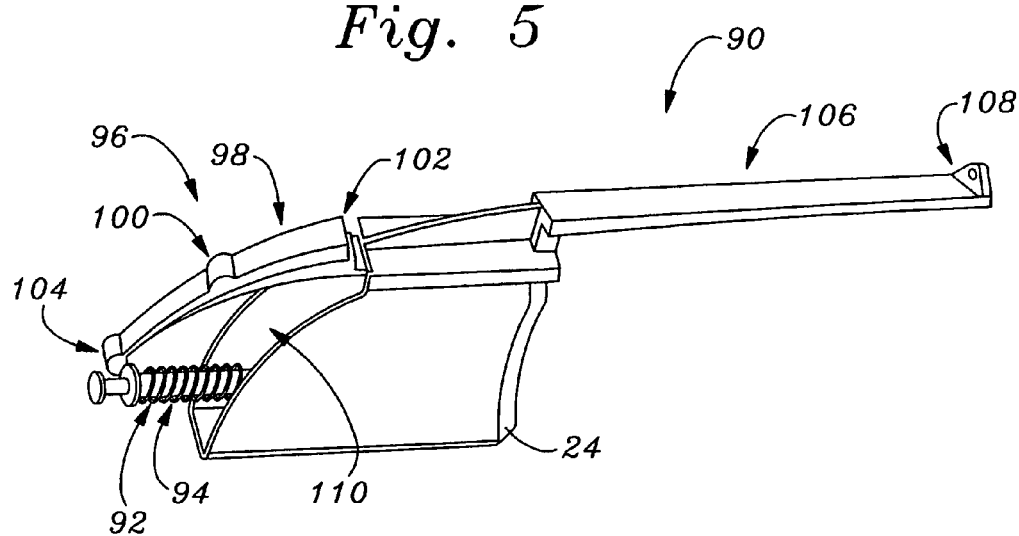
FIG. 5 shows a perspective view of the trigger assembly of the repair device of the present invention prior to actuation.
Figure 6:
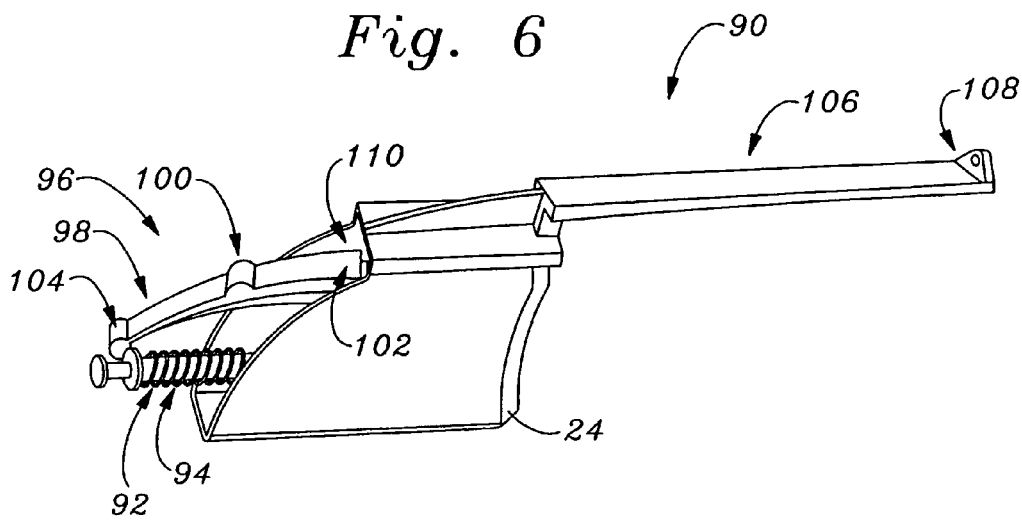
FIG. 6 shows a perspective view of the trigger assembly of the repair device of the present invention during actuation.

FIGS. 3, 5, and 6 show the various components comprising trigger assembly 90. The trigger assembly 90 includes a trigger rod 92 which in communication with the trigger 24 and includes a bias member 94, illustrated as a spring, positioned thereon. A trigger safety 96 is positioned proximate to the trigger 24 and comprises a safety body 98 having a safety actuator 100 located thereon and a trigger catch 102 capable of engaging the trigger 24. The trigger safety 96 is coupled to the repair device 10 with an attachment member 104. An actuation tray 106 having an attachment unit 108 is attached thereto is in communication with the trigger 24. FIG. 6 shows the trigger assembly 90 during actuation. As shown, during actuation the trigger safety 96 is forced to deflect downwardly by the vacuum actuator (not shown in this figure), thereby causing the trigger catch 102 to disengage the trigger 24. The trigger safety 96 enters the internal cavity 110 formed in the trigger 24 thereby, permitting the user to actuate the trigger 24 rearwardly, which results in compression of the bias member 94. Once the actuation pressure on the trigger has been released, the bias member biases the trigger 24 to a non-actuated position, thereby permitting the trigger catch 102 to re-engage the trigger 24. Those skilled in the art will appreciate the trigger safety 90 may be manufactured from a plurality of materials having sufficient resiliency to permit the repeated deflection thereof without a substantial loss of resiliency.

Figure 8:
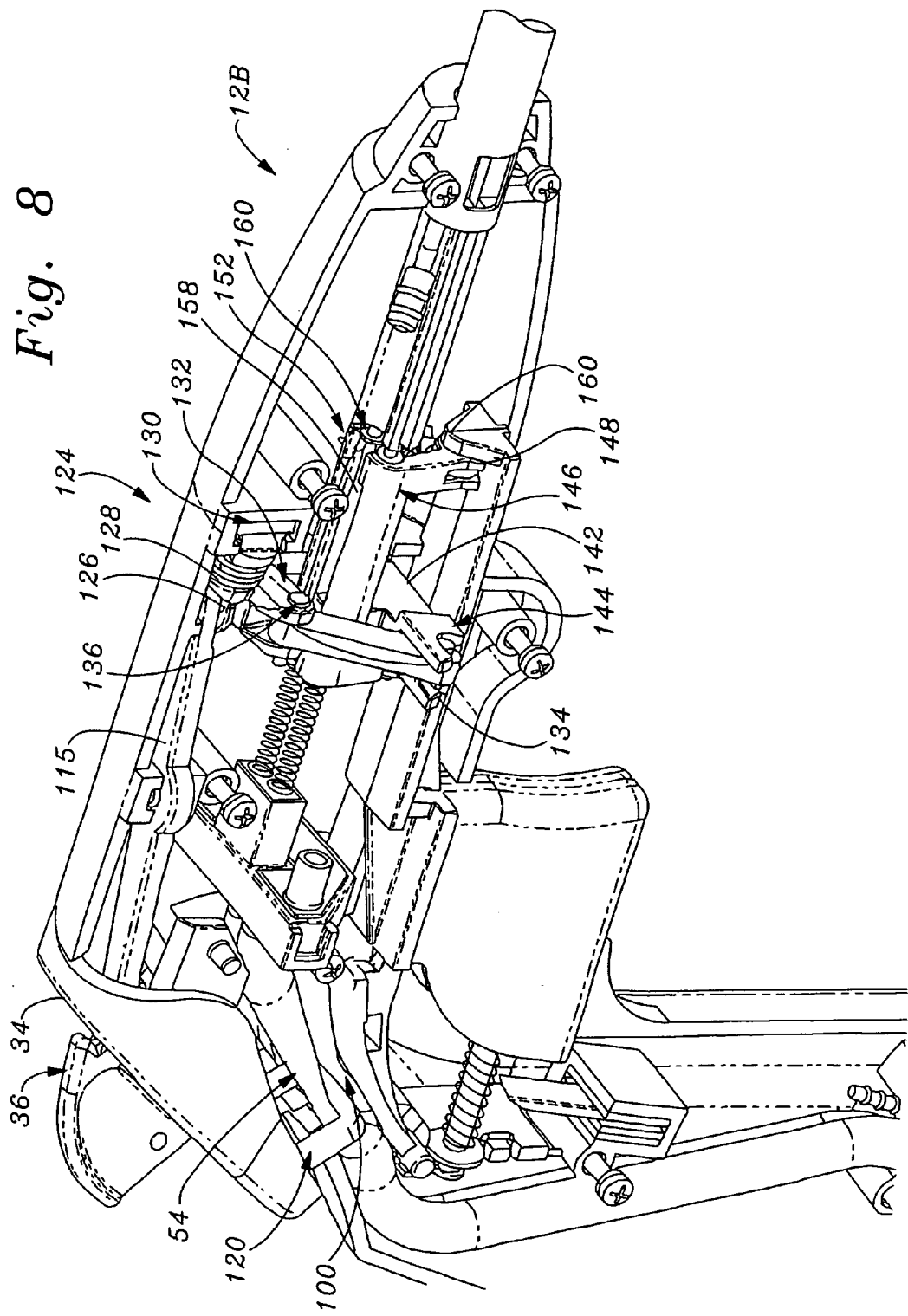
FIG. 8 shows a perspective view of the vacuum actuation assembly of the repair device of the present invention positioned within the handle portion.

FIGS. 3, 7, and 8 show the various components comprising vacuum actuator assembly 112. As shown, the vacuum actuator assembly 112 includes a vacuum actuator 34 and a vacuum selector 36 positioned on or proximate to a vacuum actuator 34. For example, a vacuum selector port 114 capable of receiving the vacuum selector 36 therein may be formed in the vacuum actuator 34. The vacuum selector 36, which is capable of a first position and a second position, is in communication with a vacuum selector shaft 115 which includes a selector pivot 116, which attaches the vacuum selector shaft to the housing body 20, and an attachment orifice 118 located near the distal end thereof. Compression member 120 capable of engaging and compressing the main vacuum line 54 is in communication with the vacuum actuator 34. Vacuum bias member 122 biases the vacuum actuator 34 outwardly. Ideally, the bias member 122 applies sufficient outward force to the vacuum actuator 34 to enable the compression member 120 to compressively squeeze the main vacuum line 54 against a stop, in this case the housing 12, to seal the main vacuum line. Those skilled in the art will appreciate that the application of inward force by the user to the vacuum actuator 34 results in the compression of the vacuum bias member 122 and causes the compression member 120 to move inwardly thereby disengaging and unsealing the main vacuum line 54. As the inward movement of the vacuum actuator 34 continues the compression member 120 engages the safety actuator 100 located on the trigger safety body 98, thereby causing the trigger safety 96 to deflect downwardly which in turn permits full actuation of the trigger 24. Thus, according to the illustrated embodiment, the trigger 24 may be actuated only when the vacuum actuator 34 is actuated.

Figure 9:
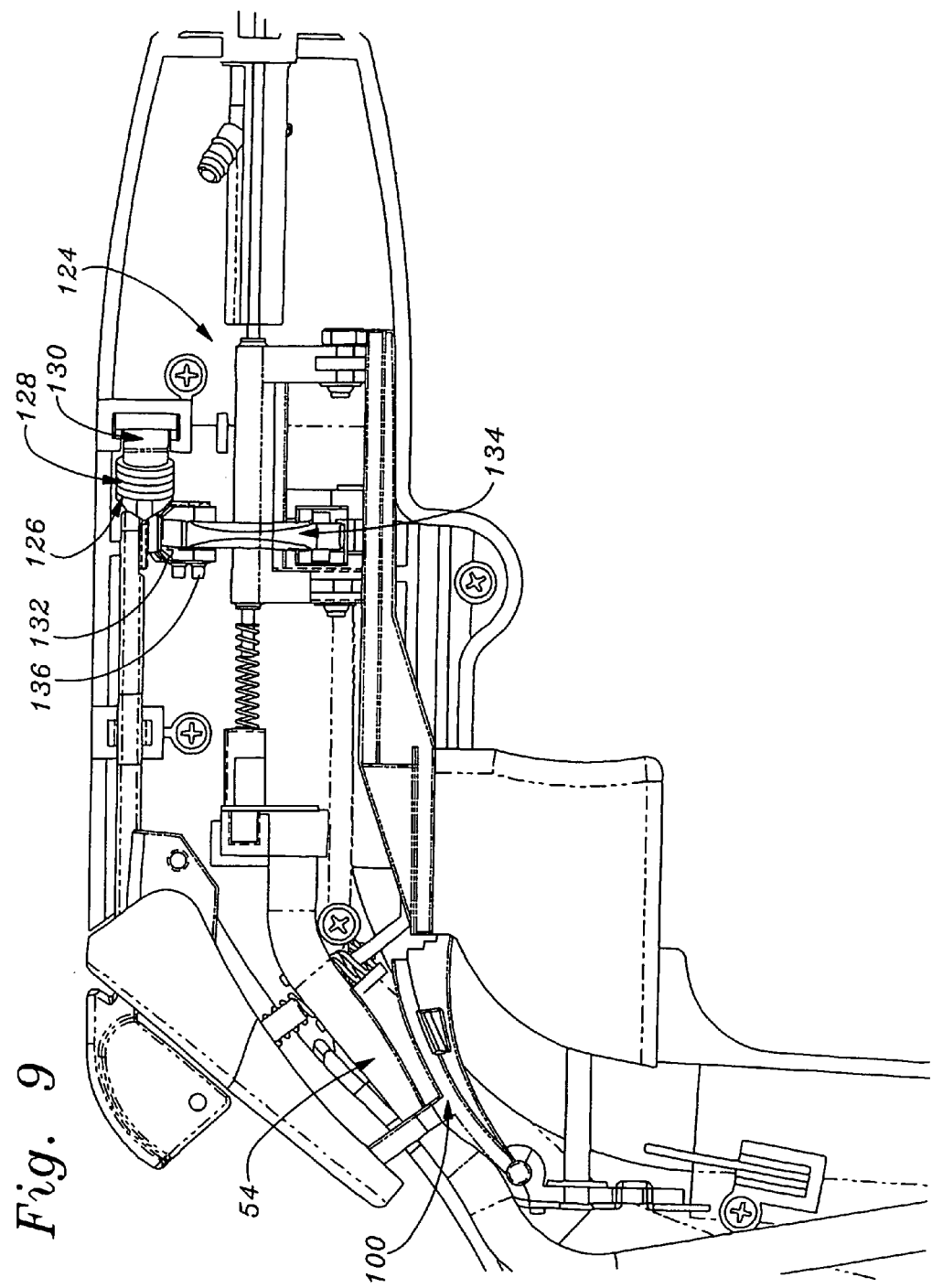
FIG. 9 shows a side view of the vacuum actuation assembly of the repair device of the present invention positioned within the handle portion.

FIGS. 3, 8, and 9 show the components of the force transmission system 124. The force transmission system 124 comprises a selector toggle 126 which is attached to or otherwise in communication with the attachment orifice 118 located on the vacuum selector shaft 114. The selector toggle 126 further includes a biasing member 128 positioned thereon, and a pivoting attachment member 130 to pivotally couple the selector toggle to the housing body 20. The force transmission system 124 further comprises a transmission bridge 132 which is in communication with the selector toggle 126. A first connecting rod 134 is attached to the transmission bridge 132 with a pivot pin 136. Similarly, a second connecting rod 138 is attached to the transmission bridge 132 with a pivot pin 140. The first and second connecting rods 134, 138 are connected to a first and second connecting rod mount 144, 150 located on a rocker bridge 142. The rocker bridge 142 is in communication with a first and second pivoting actuation member catches 146, 152, which are attached to the attachment unit 108 of the trigger actuation tray 106 with pins 148, 154. At least one actuation member is capable of engaging the first and second pivoting catches 146, 152. As shown in the present embodiment, first and second actuation members or rods 156, 158 each include at least one actuation flange 160 positioned thereon thereby forming a first capture region 162 on the first actuation member 156 and a second capture region 164 on the second actuation member 158 which are located proximate to the first and second actuation member catches 146, 152. The distal portion of the each actuation member 156, 158 is in communication with the leaflet engaging tip 16 through the elongated body 14. The proximal portion of the first and second actuation members 156, 158 includes a biasing members 166, 168, respectively. A support member 65, positioned on the vacuum manifold 64 supports the bias members 166, 168 and receives the actuation members 156, 158 during actuation.

Figure 10:
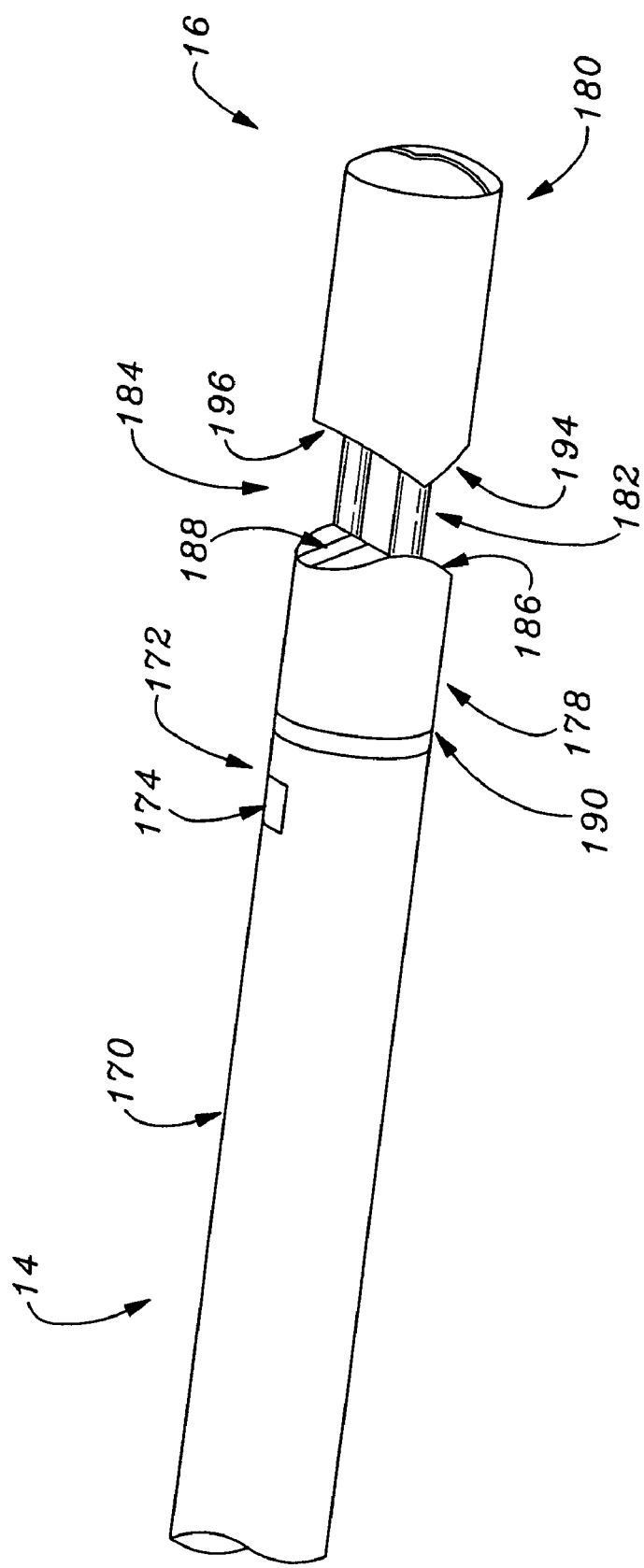
FIG. 10 shows a perspective view of the exterior of the elongated body and tissue engaging tip of the repair device of the present invention.

FIG. 10 shows the external components of the elongated body 14 and the leaflet engaging tip 16. The elongated body 14 may be manufactured from a plurality of materials in various widths and length. Those skilled in the art will appreciate that the elongated body 14 can comprise a rigid body or, in the alternative, may be manufactured from a flexible material thereby enabling the repair device 10 to be delivered through a catheter to a repair site in vivo. As shown in FIG. 10, the outer surface of the elongated body 14 comprises an outer sheath 170 capable of coupling to the handle portion 12. A guidewire retainer (not shown) may be included on the exterior surface of the outer sheath 170, the guidewire retainer (not shown) capable of engaging a guidewire (not shown) for catheter based surgical procedures. A tip retainer 172 is located on the distal portion of the outer sheath 170 of the elongated body 14. The tip retainer 172 is adapted to engage and retain the attachment device 174 of the tip engaging tip 16. Those skilled in the art will appreciate that the tip retainer 172 may include screw receivers, ports, snap fit members, or threads adapted to receive the leaflet engaging tip 16.

As shown in FIG. 10, the external components of the leaflet engaging tip 16 include a proximal portion 178 and a distal portion 180. A first and second engaging channel 182, 184 separate the proximal portion 178 from the distal portion 180. The proximal portion 178 includes a first port or vacuum recess 186 located within the first engaging channel 182. Similarly, a second port or vacuum recess 188 is located within the second engaging channel 184. The proximal portion 178 also includes a mounting member 190 capable of being sealably received within the elongated body 14, thereby effectively coupling the leaflet engaging tip 16 to the elongated body 14. The attachment device 174 may be located on or otherwise in communication with the mounting member 190 to effectuate the coupling process. Those skilled in the art will appreciate that the leaflet engaging tip 16 of the present invention may be attached to the elongated body 14 in a plurality of ways including, without limitation, detachably coupled or permanently attached.

The distal portion 180 of the leaflet engaging tip 16 includes a first and second actuation ports 194, 196 located within the first and second engaging channel 182, 184. The actuation ports 194, 196 located on the distal portion 180 are capable of passing at least one fastening device (not shown in FIG. 11) therethrough.

Figure 11:
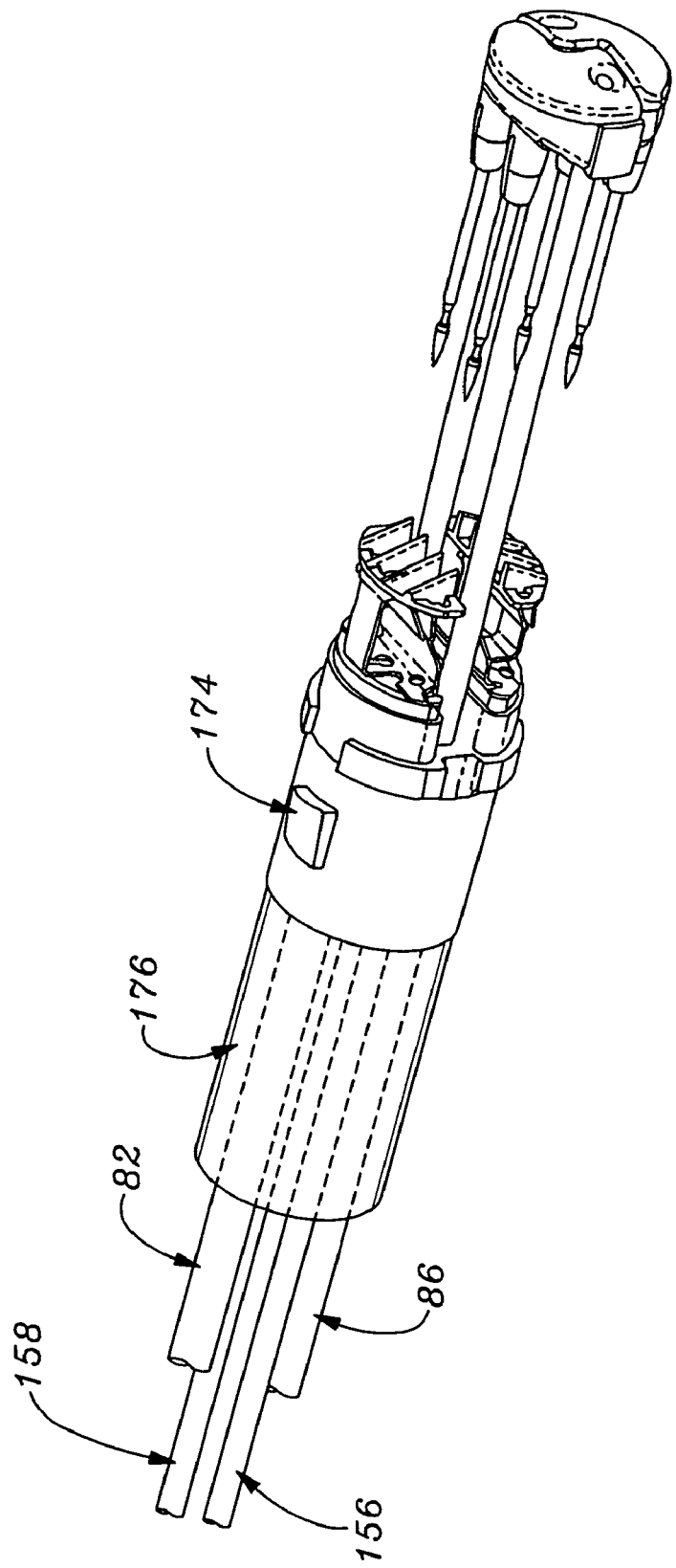
FIG. 11 shows a perspective view of the internal components of the elongated body of the repair device of the present invention.

FIG. 11 shows the internal components of the elongated body 14. As shown in FIG. 11, a first and second elongated body vacuum conduits 82, 86, respectively, and a first and second actuation members 156, 158 are located within an inner lumen 176 formed by the outer sheath 170. The first and second elongated body vacuum conduits 82, 86 are in fluid communication with the first and second vacuum conduits 72, 76 located within the housing body 20 of the handle portion 12. Similarly, the first and second actuation members 156, 158 are in communication with the force transmission system 124 positioned within the housing body 20 of the handle portion 12. The positioning conduit 78 may be positioned within the elongated body inner lumen 176.

Figure 12:
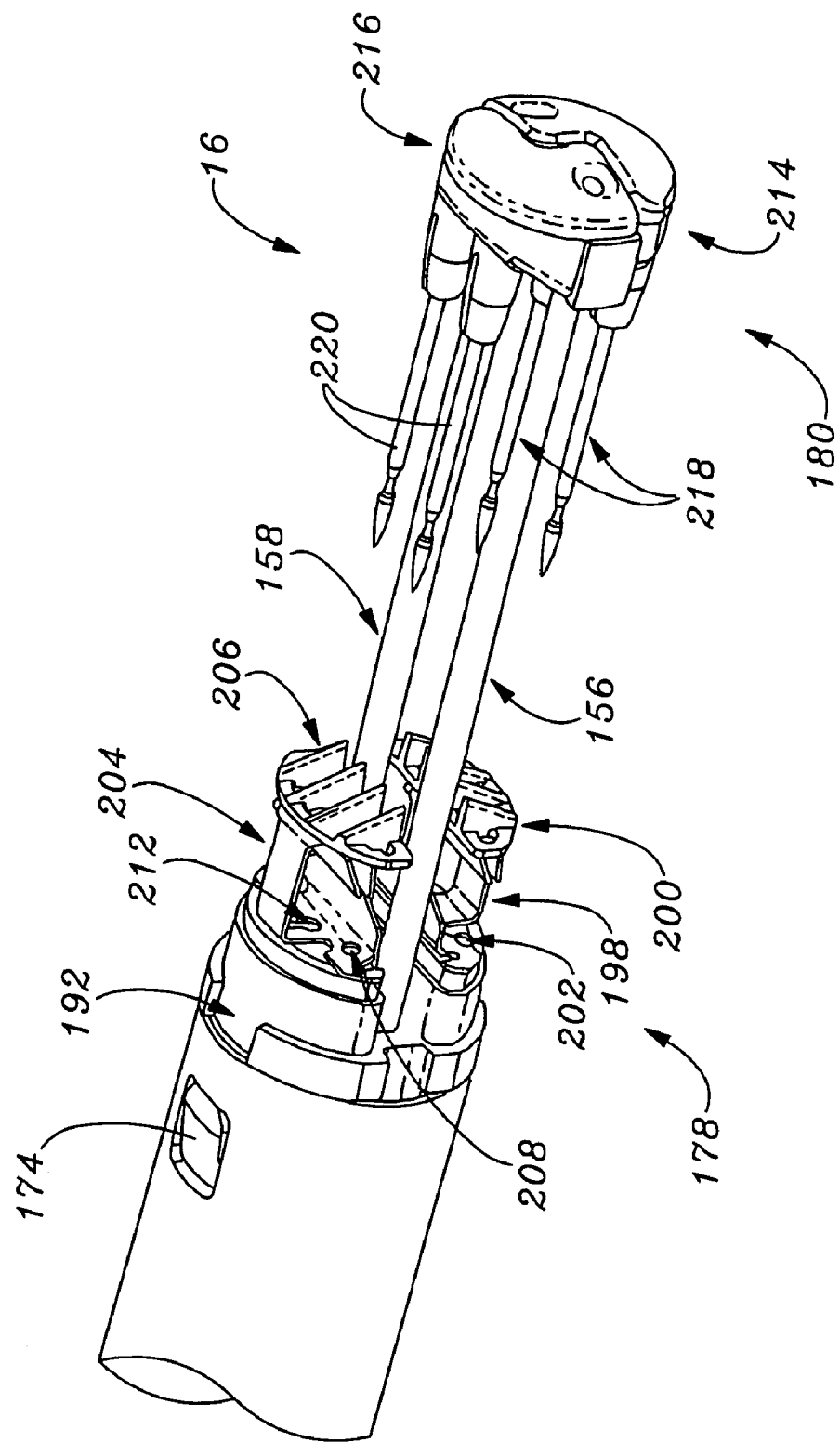
FIG. 12 shows a perspective view of the internal components of the engaging tip of the repair device of the present invention.

FIG. 12 shows the internal components of the leaflet engaging tip 16 of the present invention. A first vacuum recess device 198, which is located within the first vacuum recess 186, includes a vane member 200 capable of directing suction force through the first vacuum recess 186. At least one first fastener catch 202 is formed on or otherwise in communication with the first vacuum recess device 198. The at least one first fastener catch 202 is capable of receiving and retaining therein at least fastener device (described in more detail below). Similarly, the second vacuum recess device 204, which is located within the second vacuum recess 188, includes a vane member 206 capable of directing suction force through the second vacuum recess 188. At least one second fastener catch 208 is formed on or otherwise in communication with the second vacuum recess device 204. The at least one second fastener catch 208 is capable of receiving and retaining at least fastener device therein.

First and second vacuum ports 210, 212 (210 not visible) are located within the first and second vacuum recesses 186, 188. The first vacuum port 210 is in fluid communication with the first elongated body vacuum conduit 82, while the second vacuum port 212 is in fluid communication with the second elongated body vacuum conduit 86. A positioning port 213 in fluid communication with the positioning conduit 78 may be positioned on the proximal portion 178 or on the distal portion 180 of the engaging tip 16.

As shown in FIG. 12, the distal portion 180 of the leaflet engaging tip 16 communicates with the proximal portion 178 thereof through the first and second actuation members 156, 158. The first actuation device 214 is in communication with the first actuation member 156, while the second actuation device is in communication with the second actuation member 158. The first actuation device 214 comprises at least one fastener device 218 positioned thereon. The at least one fastener device 218 is capable of engaging the at least one first catch 202 located within the first vacuum recess 186. Similarly, the second actuation device 216 comprises at least one fastener device 220 positioned thereon. The at least one fastener device 220 is capable of engaging the at least one second catch 208 located within the second vacuum recess 188. The illustrated embodiment shows each actuation device 214, 216, respectively, having two fastener devices 218, 220, respectively, mounted thereon. Those skilled in the art will appreciate that the present invention may be manufactured with a one or more fastener devices located on the actuation devices 214, 216. The fastener devices 218, 220 may be attached to suture material (not shown) positioned within the actuation devices 214, 216. It will be appreciated that the actuation devices 214, 216 of the present invention may be actuated independently. In addition, the illustrated embodiment includes needles and suture material as tissue fasteners, but those skilled in the art will appreciate that the invention may be easily adapted to apply a plurality of fasteners. Exemplary fasteners include staples, graspers, buttons, and toggles.

Also disclosed herein is a method of using the sequential repair device of the present invention to repair discreet heart valve leaflets in vivo. While those skilled in the art will appreciate that the present invention may be adapted for use in many procedures throughout a patient's body, the inventive repair device 10 is particularly well suited for procedures to repair dysfunctional heart valves without requiring the patient's heart to be arrested. Following is a description of the inventive method for such a repair of a dysfunctional heart valve.

To use the present invention, the external vacuum conduit 52 and external positioning conduit 58 are connected to an external vacuum source (not shown) and a selected positioning device. Thereafter, the operator gains access to the repair site in vivo. For example, in procedures involving the heart, one approach to the heart requires the patient be positioned for a left anterolateral thoracotomy. An incision is made in the patient's chest and the chest is entered through the bed of the fifth rib. The pericardium is incised posterior and parallel to the left phrenic nerve, such that the incision extends from the left pulmonary artery to the apex of the left ventricle. Thereafter, a sealing cannula may be positioned on the exterior atrial wall of the patient's heart. An exemplary sealing cannula is described in U.S. patent application Ser. No. 09/800,390, entitled "Sealing Access Cannula System", filed on Mar. 5, 2001, which is incorporated herein by reference. An incision is made in the atrial tissue once the sealing cannula is sufficiently anchored to the heart wall. The leaflet engaging tip 16 of the present invention then inserted into the sealing cannula and advanced to a position proximate the mitral valve.

One embodiment of the present invention includes a pressure transducer as a positioning device. The surgeon may determine the position of the leaflet engaging tip 16 with respect to the mitral valve based on various pressure readings from the pressure transducer. For example, the operator may determine the position of the leaflet engaging tip 16 with respect to the mitral valve by observing the pressure differential between the atrium and the ventricle, as ventricular pressure within the heart is considerably greater than the pressure within the atrium.

Once the leaflet engaging tip 16 is positioned between the valve leaflets at the arterial-ventricular junction, the surgeon selects an actuation mode for the actuation system. In each successive actuation mode another leaflet, or portion of a leaflet, is to be grasped and a fastener attached thereto. The surgeon actuates the vacuum selector 36 to selectively apply a vacuum force to either the first or second vacuum recess 186, 188 located proximate to the first or second engaging channel 182, 184 (the actuated side will depend on which side the vacuum selector 36 is on). To apply suction to the first vacuum recess 186 the user positions the vacuum selector 36 to the first position, thereby causing the first pivoting catch 146 of the force transmission system 124 to engage the first capture region 162 located on the first actuation member 156. Simultaneously, the second connecting rod 138 compressively engages the second vacuum conduit 76 thereby preventing vacuum flow therethrough. Thereafter, the user depresses the vacuum actuator 34 causing the compression member 120 of the vacuum actuation assembly 112 to disengage the compressible main vacuum line 54, and permitting a vacuum flow through the first vacuum recess 186 which is in communication with the vacuum main line 54 through the first vacuum conduit 72. The valve leaflet, which is located near the first vacuum recess 186, is then captured by the vacuum force applied thereto. Once the leaflet has been captured, the user actuates the trigger assembly 90 of the repair device 10. By actuating the trigger 24, the user causes the first pivoting catch 146, which is in communication with the actuation tray 106 of the trigger assembly 90, to retract the first actuation member 156, thereby causing the first actuation device 214 of the leaflet engaging tip 16 to retract. Continued actuation of the trigger 24 causes continued rearward movement of the first actuation device 214, which results in the first fastener device 218 engaging and traversing the captured valve leaflet. Thereafter, the first fastener device(s) 218 engages a fastener catch 202 located within the first vacuum recess 186 and is retained therein. The user then releases the trigger 24, which causes the first actuation device 214 to return to the extended position. Releasing the vacuum actuator 34 halts the application of vacuum force through the first vacuum recess 186 and releases the captured valve leaflet. The suture material remains positioned through the valve leaflet where the fastener device(s) 218 had traveled therethrough.

The user may then capture another portion of the same valve leaflet, or another leaflet, by changing the actuation system to another actuation mode. To capture another leaflet the user moves the vacuum selector 36 from the first position to the second position which causes the first pivoting catch 146 to disengage the first actuation member 156 and causes the second pivoting catch 152 of the force transmission system 124 to engage the second capture region 164 located on the second actuation member 158. Simultaneously, the first connecting rod 134 compressively engages the first vacuum conduit 72 thereby preventing vacuum flow therethrough while the second connecting rod 138 disengages the second vacuum conduit 76 thereby permitting a vacuum flow therethrough. Thereafter, the user depresses the vacuum actuator 34 causing the compression member 120 of the vacuum actuation assembly 112 to disengage the compressible main vacuum line 54, and permits a vacuum flow through the second vacuum recess 188 which is in communication with the vacuum main line 54 through the second vacuum conduit 76. The valve leaflet located near the second vacuum recess 188 is then captured by the vacuum force applied thereto. Once the leaflet has been captured, the user actuates the trigger assembly 90 of the repair device. By actuating the trigger 24 the user causes the second pivoting catch 152, which is in communication with the actuation tray 106 of the trigger assembly 90, to retract the second actuation member 158 thereby causing the second actuation device 216 of the leaflet engaging tip 16 to similarly retract. Continued actuation of the trigger 24 causes continued rearward movement of the second actuation device 216 which results in the second fastener device(s) 220 engaging and traversing the captured leaflet. Thereafter, the second fastener device(s) 220 engages a second fastener catch 208 located within the second vacuum recess 188 and is retained therein. The user can then release the trigger 24 thereby returning the second actuation device 216 to an extended position. Release of the vacuum actuator 34 halts the application of vacuum force and releases the valve leaflet. The suture material remains positioned through the valve leaflet where the fastener device(s) 220 had traveled therethrough.

The user can remove the repair device 10 from the patient's heart. The suture material, which has been positioned through various portions of the valve tissue remains in place while the extraneous suture material is feed from the repair device 10 during removal. Thereafter, a surgical knot may be formed in the extraneous suture material and advanced to an area within the heart using a surgical knot pusher, thereby approximating the valve leaflet tissue. Once the final knot is applied to the area of interest the extraneous suture material is trimmed and the various incisions are closed.

In closing, it is noted that specific illustrative embodiments of the invention have been disclosed hereinabove. It is to be understood that the invention is not limited to these specific embodiments. This specification has focused on the application of the present inventive devices and methods to the repair of heart valve leaflets. However, one of skill in the art will appreciate that the disclosed devices and methods could alternatively be used to approximate any two pieces of tissue throughout a patient's body. For example, the present invention may also used to repair Arterial Septal Defects (ASD), Ventricular Septal Defects (VSD), and defects associated with Patent Foramen Ovale (PFO). Accordingly, it should be recognized that the references to "leaflets" throughout could be equally substituted for other tissue segments that might require similar approximation procedures.

With respect to the claims, it is applicant's intention that the claims not be interpreted in accordance with the sixth paragraph of 35 U.S.C. § 112 unless the term "means" is used followed by a functional statement. Further, with respect to the claims, it should be understood that any of the claims described below can be combined for the purposes of the invention.

What is claimed is:

1. A method for repairing a heart valve having multiple leaflets, comprising:
providing a repair device having a deployment mechanism for independently applying first and second fastener elements to first end second heart valve leaflets, respectively;
stabilizing the first leaflet with vacuum force from the repair device;
deploying the first fastener element into the stabilized first leaflets;
disengaging the first leaflet from the repair device while leaving the first fastener element deployed therein;
stabilizing the second leaflet with vacuum force from the repair device, wherein stabilizing the second leaflet occurs after deploying the first tissue fastener element and disengaging the first leaflet;
deploying the second fastener element into the stabilized second leaflet;
disengaging the second leaflet from the repair device while leaving the second fastener element deployed therein; and
joining the first and second leaflets by reducing the distance between the first and second fastener elements.

2. The method of claim 1 further comprising controllably and selectively stabilizing the first and second leaflets with vacuum force.

3. The method of claim 1 wherein the first and second fastener elements are portions of a piece of suture material and wherein the step of reducing the distance between the first and second fastener elements is performed by tying the suture material into a knot.

4. The method of claim 1 further comprising adjusting the position of the repair device relative to the leaflets by monitoring fluid pressure around a distal end of the repair device.

5. The method of claim 4 wherein the adjusting step is performed while the distal end of the repair device is in an atrial-ventricular junction and wherein the monitor step is performed by observing pressure differentials between blood in an adjacent ventricle and an adjacent atrium.

6. The method of claim 1 wherein the first and second fastener elements are portions of a piece of suture material and wherein the step of reducing the distance between the first and second fastener elements is performed by drawing together portions of the suture material and trimming any extraneous suture material.

7. A method for repairing a heart valve having multiple leaflets, comprising:
providing a repair device having a deployment mechanism for independently applying first and second fastener elements to first and second heart valve leaflets, respectively;
advancing a distal portion of the repair device to a position adjacent the first leaflet;
stabilizing the first leaflet with the repair device by applying a vacuum force to the distal portion of the repair device;
deploying the first fastener element into the stabilized first leaflet;
disengaging the first leaflet from the repair device while leaving the first fastener element deployed therein;
stabilizing the second leaflet with the repair device by applying a vacuum force to the distal portion of the repair device, wherein stabilizing the second leaflet occurs after deploying the first tissue fastener element and disengaging the first leaflet;

deploying the second fastener element into the stabilized second leaflet;

disengaging the second leaflet from the repair device while leaving the second fastener element deployed therein; and joining the first and second leaflets by reducing the distance between the first and second fastener elements.

8. The method of claim 7, wherein the distal portion of the repair device has a first vacuum port, and the step of stabilizing the first leaflet comprises applying a vacuum force to the first vacuum port.

9. The method of claim 8, wherein the distal portion of the repair device has a second vacuum port, and the step of stabilizing the second leaflet comprises applying a vacuum force to the second vacuum port.

10. The method of claim 9, wherein the step of stabilizing the first leaflet comprises applying a vacuum force to the first vacuum port while simultaneously preventing the application of a vacuum force to the second vacuum port.

11. The method of claim 7, wherein the first and second fastener elements are portions of a piece of suture material.

12. A method for treating tissue, comprising:
providing a repair device having a deployment mechanism for independently applying first and second fastener elements to first and second tissue pieces, respectively;

advancing the repair device to a position adjacent the first tissue piece;

stabilizing the first tissue piece by applying a vacuum force with the repair device;

deploying the first fastener element into the stabilized first tissue piece;

disengaging the first tissue piece from the repair device while leaving the first fastener element deployed therein;

stabilizing the second tissue piece with the repair device, wherein stabilizing the second tissue piece by applying a vacuum force occurs after deploying the first tissue fastener element and disengaging the first tissue piece;

deploying the second fastener element into the stabilized second tissue piece; and disengaging the second tissue piece from the repair device while leaving the second fastener element deployed therein.

13. The method of claim 12, wherein the first and second fastener elements are portions of a piece of suture material, and the method further comprises:
joining the first and second tissue pieces by drawing together portions of the suture material.

14. The method of claim 13, comprising:
trimming any extraneous suture material from the piece of suture material, the trimming of extraneous suture material occurring after drawing together portions of the suture material.

15. The method of claim 12, wherein the repair device has a first vacuum port, and the step of stabilizing the first tissue piece comprises applying the vacuum force to the first vacuum port.

16. The method of claim 15, wherein the repair device has a second vacuum port, and the step of stabilizing the second tissue piece comprises applying the vacuum force to the second vacuum port.

17. The method of claim 16, wherein the step of stabilizing the first tissue piece comprises applying the vacuum force to the first vacuum port while simultaneously preventing the application of the vacuum farce to the second vacuum port.

18. A method for repairing a mitral valve in a human heart, comprising:
providing a repair device having a handle portion along a proximal end and an elongated body extending distally from the handle portion, the elongated body having a leaflet engaging tip and a deployment mechanism for independently applying first and second fastener elements to first and second heart valve leaflets respectively;

positioning the leaflet engaging tip adjacent to the first leaflet in the mitral valve;

applying a first vacuum force along the leaflet engaging tip for capturing and holding only the first leaflet;

deploying the first fastener element from the leaflet engaging tip and through a portion of the first leaflet while holding the first leaflet;

halting the first vacuum force and thereby releasing the first leaflet from the leaflet engaging tip;

positioning the leaflet engaging tip adjacent to the second leaflet in the mitral valve;

applying a second vacuum force along the leaflet engaging tip for capturing and holding only the second leaflet;

deploying the second fastener element from the leaflet engaging tip and through a portion of the second leaflet while holding the second leaflet;

halting the vacuum force and thereby releasing the second leaflet from the leaflet engaging tip; and pulling the first and second leaflets into closer proximity by reducing a distance between the first and second fastener elements;

wherein each of the above steps for repairing the mitral valve is performed substantially in the order recited.

19. The method of claim 18, wherein the first and second fastener elements are portions of a piece of suture material.

20. The method of claim 18, wherein the leaflet engaging tip of the repair device is removed from the mitral valve before pulling the first and second leaflets into closer proximity.

21. A method for repairing a biological valve, comprising:
advancing an elongated body to a treatment site adjacent to a biological valve, the elongated body having a leaflet engaging tip and a deployment mechanism for independently applying first and second portions of an attachment mechanism to first and second valve leaflets, respectively;

applying a vacuum force along the leaflet engaging tip for capturing only the first leaflet;

coupling the first portion of the attachment mechanism to the first leaflet;

halting the vacuum force and thereby releasing the first leaflet from the leaflet engaging tip;

applying the vacuum force along the leaflet engaging tip for capturing only the second leaflet;

coupling the second portion of the attachment mechanism to the second leaflet;

halting the vacuum force and thereby releasing the second leaflet from the leaflet engaging tip; and pulling the first and second leaflets into closer proximity by manipulation of the attachment mechanism;

wherein the second leaflet is captured only after coupling the first portion of the attachment mechanism to the first leaflet and releasing the first leaflet.

* * * * *

UNITED STATES PATENT AND TRADEMARK OFFICE
CERTIFICATE OF CORRECTION

PATENT NO. : 7,094,244 B2 Page 1 of 1
APPLICATION NO. : 10/106583
DATED : August 22, 2006
INVENTOR(S) : Schreck It is certified that error appears in the above-identified patent and that said Letters Patent is hereby corrected as shown below:

Column 14, Claim 1, line 9 after "first" please delete "end" and insert --and--.

Column 14, Claim 1, line 14 please delete "leaflets" and insert --leaflet--.

Column 16, Claim 17, line 2 after "vacuum" please delete "farce" and insert --force--.

Signed and Sealed this

Nineteenth Day of February, 2008

JON W. DUDAS
*Director of the United States Patent and Trademark Office*